US006715188B1

(12) United States Patent
Jackson et al.

(10) Patent No.: US 6,715,188 B1
(45) Date of Patent: Apr. 6, 2004

(54) HINGED TAB FOR SLOT AND TAB CLOSURE SYSTEMS

(75) Inventors: Byron M. Jackson, Forest Lake, MN (US); Leigh E. Wood, Woodbury, MN (US); Randall L. Alberg, Maplewood, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/253,171

(22) Filed: Sep. 24, 2002

(51) Int. Cl.[7] .................. A44B 21/00; B65D 63/00; C09J 7/02
(52) U.S. Cl. .................. 24/698.1; 24/72.5; 24/304; 24/321; 604/387; 604/390; 604/391
(58) Field of Search .................. 24/304, 306, 321, 24/318, 16 PB, 17 B, 500, 698.1; 604/387, 389, 390, 391

(56) References Cited

U.S. PATENT DOCUMENTS

| 198,097 | A | | 12/1877 | Fries |
|---|---|---|---|---|
| 207,253 | A | | 8/1878 | Chipley |
| 378,874 | A | | 3/1888 | Davis |
| 771,719 | A | | 10/1904 | Copeland |
| 791,654 | A | | 6/1905 | Searle |
| 1,095,947 | A | | 5/1914 | Thorp |
| 1,499,428 | A | | 7/1924 | Wagner |
| 1,829,613 | A | * | 10/1931 | Sato ............... 402/15 |
| 2,294,617 | A | | 9/1942 | Horowitz |
| 2,548,162 | A | | 4/1951 | Karels |
| 2,787,244 | A | | 4/1957 | Hickin |
| 2,837,096 | A | | 6/1958 | Leveillee |
| 3,276,944 | A | | 10/1966 | Levy |
| 3,338,992 | A | | 8/1967 | Kinney |
| 3,341,394 | A | | 9/1967 | Kinney |
| 3,482,289 | A | | 12/1969 | Stradella |

(List continued on next page.)

FOREIGN PATENT DOCUMENTS

| CA | 2128124 | 1/1995 |
|---|---|---|
| CA | 2240032 | 1/1999 |
| EP | 0 757 550 B1 | 12/1998 |
| GB | 493 819 | 10/1938 |
| GB | 2 284 742 | 6/1995 |
| GB | 2 328 365 B | 12/1999 |
| WO | WO 96/10481 | 4/1996 |
| WO | WO 97/02795 | 1/1997 |
| WO | WO 97/02797 | 1/1997 |
| WO | WO 97/02799 | 1/1997 |
| WO | WO 97/07319 | 2/1999 |
| WO | WO 00/35395 | 6/2000 |
| WO | WO 01/58402 A1 | 8/2001 |

*Primary Examiner*—Victor Sakran
(74) *Attorney, Agent, or Firm*—Gary L. Griswold; Robert W. Sprague; William J. Bond (57) ABSTRACT

There is provided an improved tab member for a closure system comprising a tab portion and a slot member. The slot member includes a slit or a loop, with the slot located between an inboard portion and an outboard portion. The tab portion has a tab member having a length, an inner edge, an outer edge and at least one lip portion. The tab member outer edge is passed through the slot of the slot member to engage the fastening device. Once passed through the slot, at least one lip portion of the tab member overlaps or catches the outboard portion of the slot member to prevent the tab member from disengaging from the slot member. The slot member outward portion is retained between the lip portion (s) and the underlying generally flexible tab carrier substrate.

16 Claims, 7 Drawing Sheets

U.S. PATENT DOCUMENTS

| | | |
|---|---|---|
| 3,502,538 A | 3/1970 | Petersen |
| 3,502,763 A | 3/1970 | Hartmann |
| 3,542,615 A | 11/1970 | Dobo et al. |
| 3,620,180 A | 11/1971 | Waldes |
| 3,692,618 A | 9/1972 | Dorschner et al. |
| 3,694,867 A | 10/1972 | Stumpf |
| 3,834,824 A | 9/1974 | Jahn |
| 4,001,924 A | 1/1977 | Bengtsson |
| 4,223,059 A | 9/1980 | Schwarz |
| 4,340,563 A | 7/1982 | Appel et al. |
| 4,761,322 A * | 8/1988 | Raley .................. 428/198 |
| 4,906,492 A | 3/1990 | Groshens |
| 4,965,122 A | 10/1990 | Morman |
| 4,981,747 A | 1/1991 | Morman |
| 5,019,071 A | 5/1991 | Bany et al. |
| 5,114,781 A | 5/1992 | Morman |
| 5,116,662 A | 5/1992 | Morman |
| 5,167,897 A | 12/1992 | Weber et al. |
| 5,176,671 A * | 1/1993 | Roessler et al. ......... 604/391 |
| 5,226,992 A | 7/1993 | Morman |
| 5,264,264 A * | 11/1993 | Shibata et al. ......... 428/41.8 |
| 5,300,057 A | 4/1994 | Miller et al. |
| 5,389,438 A | 2/1995 | Miller et al. |
| 5,403,302 A * | 4/1995 | Roessler et al. ......... 604/391 |
| 5,501,679 A | 3/1996 | Krueger et al. |
| 5,545,159 A | 8/1996 | Lancaster et al. |
| 5,591,521 A * | 1/1997 | Arakawa et al. ......... 428/352 |
| 5,685,758 A | 11/1997 | Paul et al. |
| 5,944,707 A | 8/1999 | Ronn |
| 5,970,585 A * | 10/1999 | Scholey .................. 24/482 |
| 6,022,431 A | 2/2000 | Blenke et al. |
| 6,044,526 A * | 4/2000 | Putney .................. 24/72.5 |
| 6,093,665 A | 7/2000 | Sayovitz et al. |
| 6,102,901 A | 8/2000 | Lord et al. |
| 6,251,097 B1 | 6/2001 | Kline et al. |
| 6,261,278 B1 | 7/2001 | Chen et al. |
| 6,432,098 B1 | 8/2002 | Kline et al. |

* cited by examiner

HINGED TAB FOR SLOT AND TAB CLOSURE SYSTEMS

FIELD OF THE INVENTION

The present invention relates to macromechanical closure elements for disposable articles such as diapers, training pants and incontinence pads. More particularly, the present invention relates to closure elements for disposable articles which are easy to use and manufacture.

BACKGROUND OF THE INVENTION

Many different types of refastenable closure elements are known, including ties, pins, hook and loop systems, hook and eye systems, buttons, snaps, interlocking shapes, buckles, adhesive tapes, cohesive surfaces, and zippers and other slide connectors. Such fasteners have been used on a variety of products, both durable and disposable. Typical uses include envelopes, clothing, diapers, packages, footwear, construction closures, general attachment needs and feminine hygiene products.

Some fastening devices, such as hook and loop or adhesive tapes, require aligning an engaging surface with a landing surface. While this can result in an effective closure, it often results in misapplication and/or poor alignment of the elements being connected. Further, hook and loop fasteners can become ineffective due to compression and contamination or can harm surrounding materials. With an adhesive system, improperly fastening the device may render the entire product unusable. For example, in diaper applications, repositioning a tape tab which has been fastened improperly may result in tearing the outer cover of the diaper. Further, adhesive systems are prone to contamination-induced performance problems. In order to help prevent such problems, the use of these types of fasteners often require inefficient designs and extra material usage which can add to the cost of the products.

Other systems such as buttons, snaps, hooks and eyes, and ties are limited in that they connect discrete points only. If only one fastening device is used for a particular closure, the connection allows material around the fastener to rotate around the discrete points connected by the fastener. Further, if a span other than a single point needs to be connected, these systems generally require more than one fastening device per closure. Multiple connections can be cumbersome and can result in gapping between the discrete fastening device components, particularly if the connection is under stress. These systems also require precise alignment of the components to create the connection desired. Some point-to-point fastening systems require that forces be maintained on the system throughout the time the fastener is connected.

Other examples of interlocking closures can be found in U.S. Pat. Nos. 198,097; 207,253; 378,874; 771,719; 791,654; 2,837,096; 3,482,289; 3,620,180; 3,834,824 and 4,001,924. All of these fasteners can join lengths or spans, but each suffers from at least one important disadvantage, especially for use with disposable products like diapers. Some require the user to press on the connection to create engagement. Others require intricate manipulation to engage, such as tucking a tab over one element then below another. Yet others require at least one element to deform to create engagement, which may limit the load bearing capability of the fastener. Most lack provisions for allowing the fastener to conform to different shaped surfaces while in use and many of the systems have no provisions allowing for adjustable fit. Further, if used in disposable absorbent products such as diapers, these fasteners can cause skin marking and discomfort for the wearer.

To address these problems, U.S. Pat. No. 6,251,097 discloses a slot and tab closure design wherein the tab hinges are a "T" shape. The tabs are specifically designed for use on disposable diapers, bibs, wraps and packages, as well as sanitary napkins. The tabs taught in this patent contain a "lip" portion, defined as that portion of the tab member 42 which is not joined directly to the underlying structure of the article to which the tab member is attached, and the lip portion lifts away from the underlying structure of the article so that it can be positioned in an overlapping configuration with at least a portion of an outboard portion of a slot member. This lip portion in the tab requires a complex product process as the lip is formed of a separate material attached to the underlying support substrate.

WO 97/02795 discloses a closure system on a diaper, which could also be considered a macro closure. The fastening means is comprised of two mutually co-acting first and second fastener elements and characterized in that the first or the second part of the fastener means includes a fastener portion which projects out in the circumferential direction of the waist band and which can be inserted into an opening in its associated second or first fastener element, and in that one of the first and the second fastener elements includes at least one locking member which extends in a direction generally perpendicular to the direction in which the fastener portion is inserted and co-acts with a locking aperture in the second fastener element when in the inserted position. The closure system requires complex three-dimensional shapes and would be difficult to manufacture and provide in a packaged form with multiple diapers.

U.S. Pat. No. 2,548,162 teaches a pinless diaper that uses what can be called a macro closure system. This system uses tabs and loops and the tabs are heart shaped and the widest part of the tab exceeds substantially in width the base portion (where the tab attaches to the diaper).

U.S. Pat. No. 5,545,159 teaches a disposable diaper with a type of macro closure wherein the macro closure comprises interlocking projections and receptacles. This system is also complex.

There is a need in the art for a macro closure system where the elements are easy to manufacture and use as well as can be packaged into a multi-article pack without creating uniformity problems due to the component having a three dimension shape.

SUMMARY OF THE INVENTION

The present invention is directed at an improved tab member for a closure system comprising a tab portion and a slot member. The slot member includes a slit or slot, with the slot located between an inboard portion and an outboard portion. The tab portion has a tab member having a length, an inner edge, an outer edge and at least one lip portion. The tab member outer edge is passed through the slot of the slot member to engage the fastening device. Once passed through the slot, at least one lip portion of the tab member overlaps or catches the outboard portion of the slot member to prevent the tab member from disengaging from the slot member. The slot member outward portion is retained between the lip portion(s) and an underlying tab substrate.

The improved tab portion of the present invention is a folded structure with at least one layer in common with the tab member and the tab substrate which carries the tab member. This provides a strong connection between the tab member and the tab substrate as the overall tab portion is substantially formed of a single substrate or laminate. The invention tab portion is also simple to manufacture using standard folding and laminating techniques.

DETAILED DESCRIPTION OF THE PREFERRED EMBODIMENT

Figure 1:
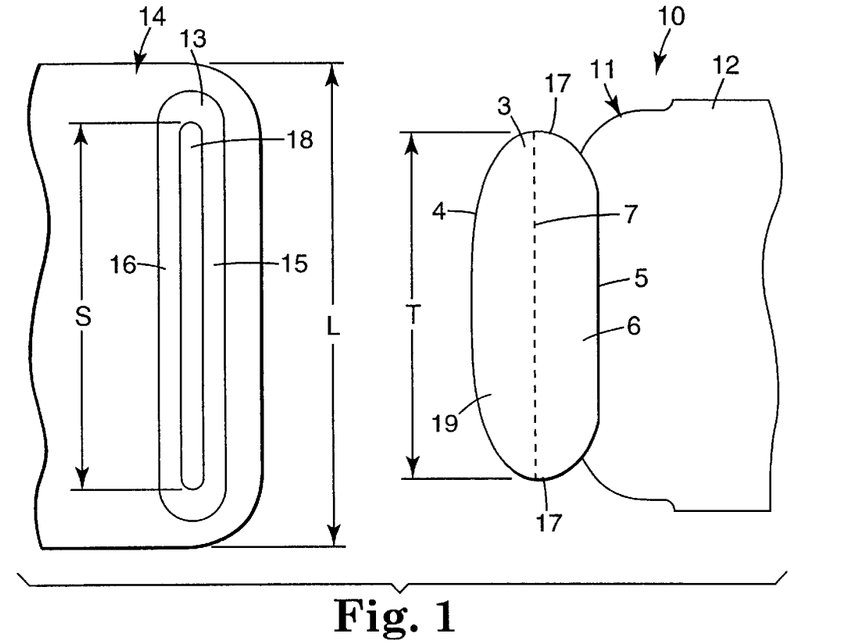
FIG. 1 is a top view of an invention macro closure system tab portion prior to use with a slot member.

The fastening system of the invention preferably includes a fastening device, which comprises at least a tab portion and a slot member. As shown in FIG. 1, the tab portion 11 preferably includes a generally elongate tab member 3, having an outer edge 4, an inner edge 5, at least one lip portion 6 and a length T, and a tab substrate 12. The slot member 14 includes an inboard portion 16, an outboard portion 15 and a slot 18 disposed between the inboard portion 16 and the outboard portion 15. The slot member 14 has a length L and the slot 18 has a length S, as shown in FIG. 1. The slot length S, is preferably greater than or equal to the tab length T. However, preferably it is only up to 10 percent greater than the tab length T.

Figure 2:
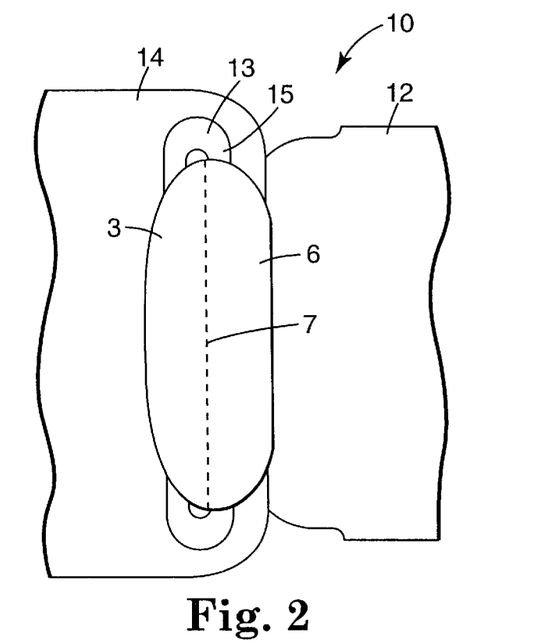
FIG. 2 is a top view of an invention macro closure system tab portion in use with a slot member.

The fastening device 10 is fastened by passing the tab member 3 completely through the slot 18 of the slot member 14 (It is also contemplated that two or more slot members could engage with two or more tab members.). Once the tab member 3 has been passed through the slot 18, as shown in FIG. 2, the lip portion or portions 6 of the tab member 3 rotate into a plane generally parallel with the plane of the slot member 14 such that at least a part of a lip portion 6 overlaps at least a part of an outboard portion 15 of the slot member 14. The lip portion 6 of the tab member 3 in combination with the tab substrate 12 will prevent the tab member 3 from slipping back through the slot 18 and disengaging the fastening device 10. The material forming the slot 13 will act to resist forces in shear, which tend to direct the tab member 3 and the slot member 14 apart.

Figure 3:
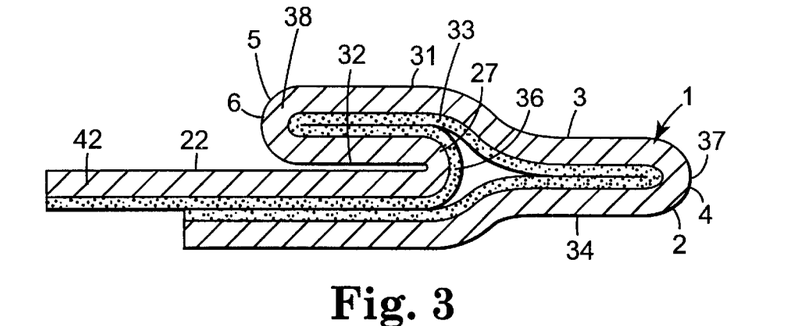
FIG. 3 is a cutaway side view of a first embodiment precursor web from which the invention tab portions are cut.
Figure 4:
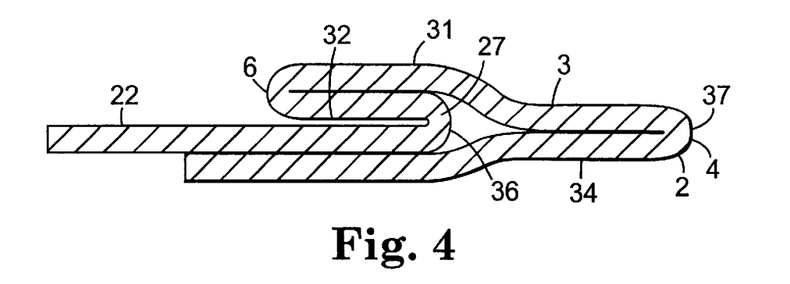
FIG. 4 is a cutaway side view of a second embodiment precursor web from which the invention tab portions are cut.
Figure 5:
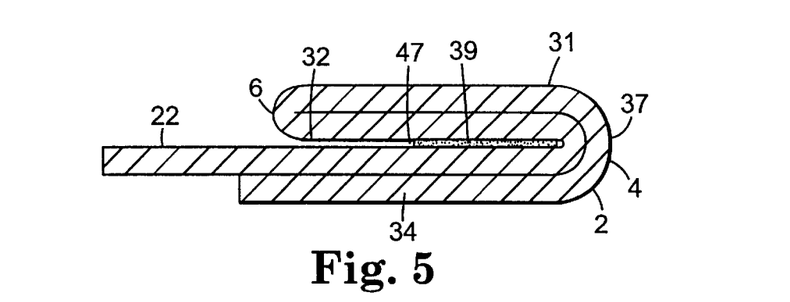
FIG. 5 is a cutaway side view of a third embodiment precursor web from which the invention tab portions are cut.
Figure 6:
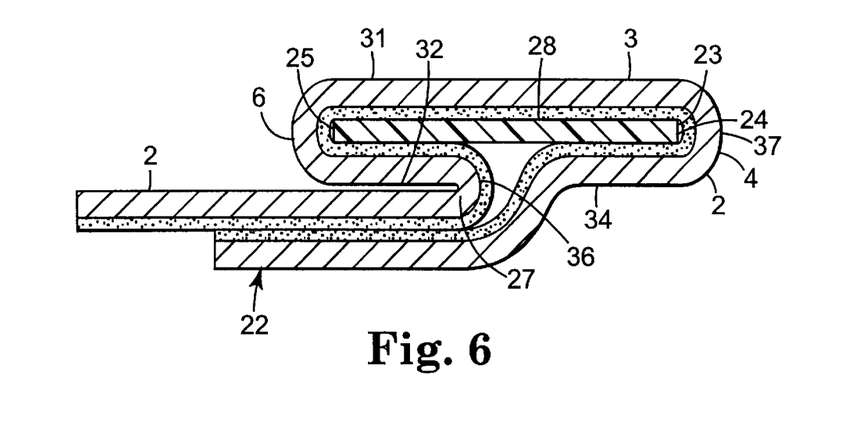
FIG. 6 is a cutaway top view of a fourth embodiment precursor web from which the invention tab portions are cut using a reinforcement element.

As shown in FIG. 1, the tab member 3 is preferably an elongated member having a length T, an inner edge 5, an outer edge 4, and a lip portion 6 generally adjacent at least a portion of the inner edge 5. The tab member preferably has longitudinal ends 17 and a central region 19. The lip portion 6 is that portion of the tab member 3, which can rotate at a pivot region 7 away from the plane of the tab substrate 12. A layer forming at least in part the tab substrate 12 also forms the tab member 3. As shown in FIG. 3, this common layer is folded to form at least the lip portion 6 with an outer fold 38 forming inner edge 5 and an inner fold 36 creating the lip portion 6. The outer edge 4 can also be an outer fold 37 or can be cut from a folded portion. The lip portion 6 lifts away from the tab substrate 12 or 22 forming a V-shaped catching surface. The bottom leg of the V is formed by the tab substrate 12 or 22 and the upper portion of the leg of the V is formed by the tab member 3 lip portion 6. The lip portion 6 of the tab member 3 is folded from a material or laminate layer also forming the tab substrate 12 or 22. A pivot region 7, 27 or 47 is formed by the inner fold 36 as shown in FIGS. 3, 4 or 6 or bonding 39 between the adjacent layers of an inner fold as shown in FIG. 5.

The tab substrate 12 and 22 and tab member may be made from any suitable rigid or semi-rigid material. Generally, however, the tab member 3 should be sized to fit through the slot of the slot member with little or no bending or deformation of either component. The shape of the tab member will often be dependent on the end use of the fastening device, but in any case should be aesthetically pleasing, easy to hold and maneuver, and capable of maintaining the device in a fastened configuration throughout the intended period of use when subjected to expected forces and external conditions.

Figure 8:
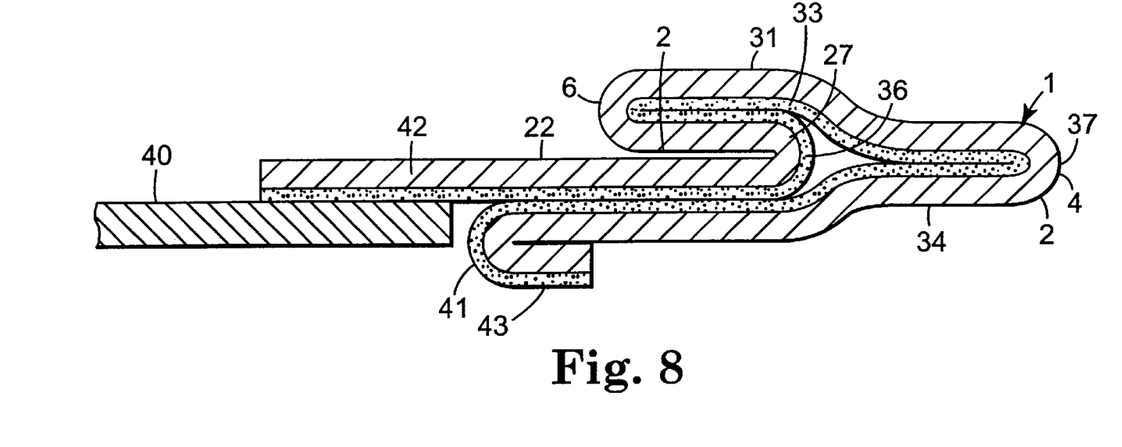
FIG. 8 is a side view of the fifth embodiment tab portion of FIG. 5 attached partially to an article.
Figures 9, 10:
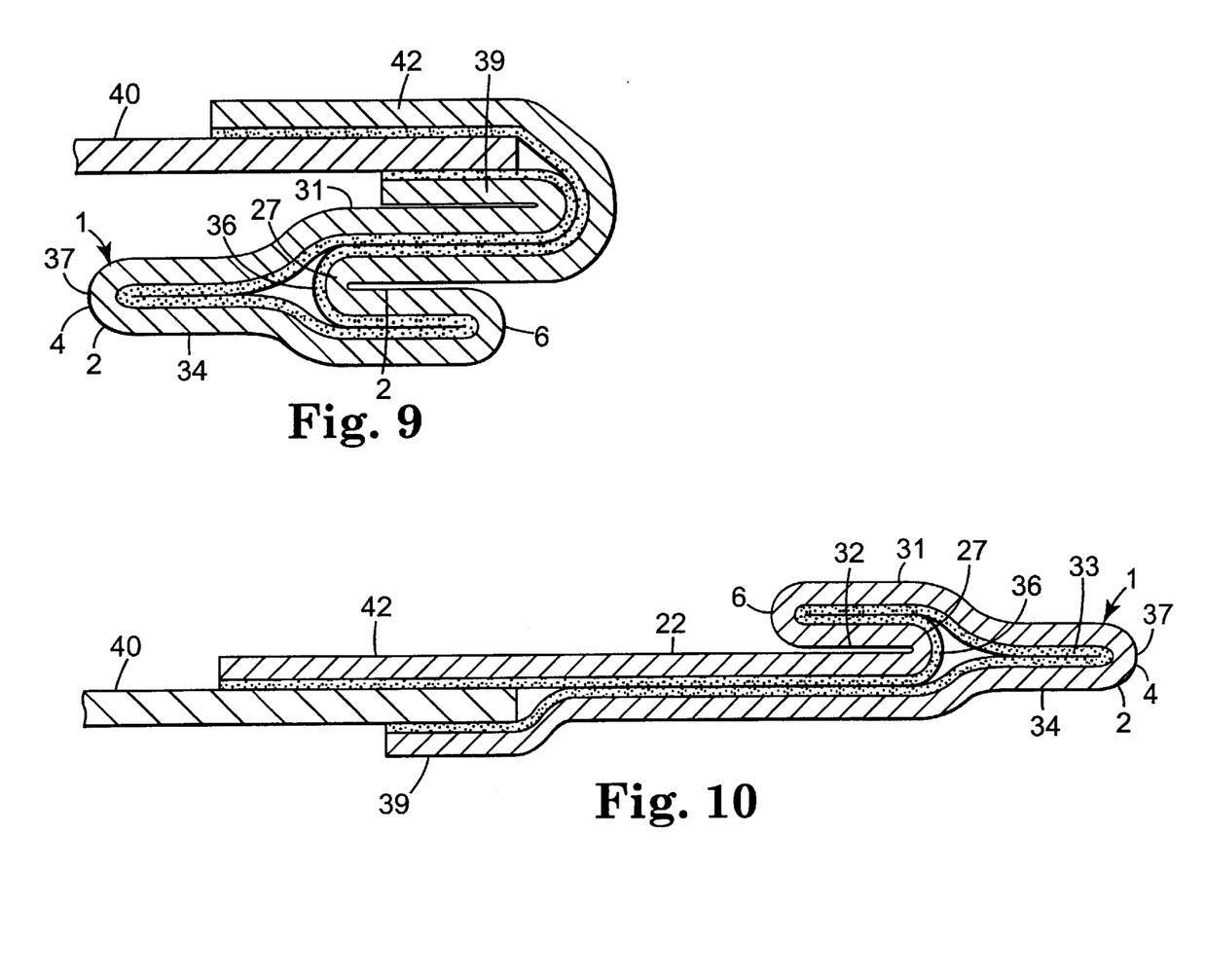
FIG. 9 is a side view of the fifth embodiment tab portion fully attached to an article.
FIG. 10 is side view of the fifth embodiment tab portion fully extended for use.
Figure 13:
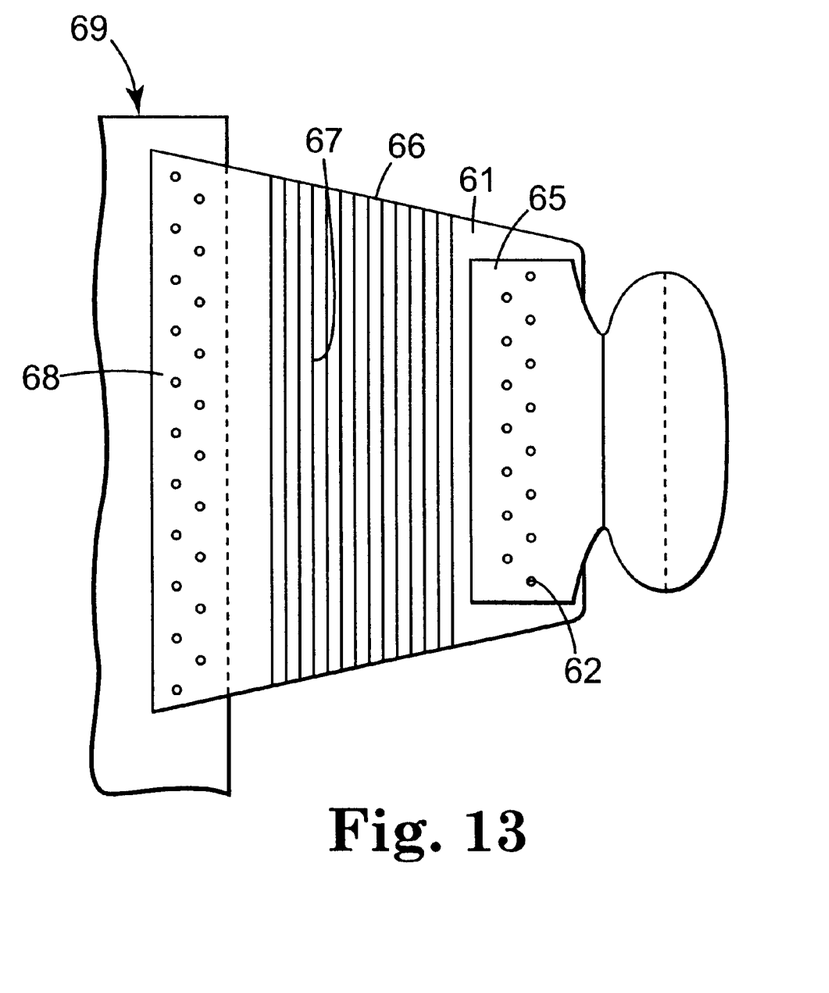
FIG. 13 is a top view of an invention tab portion attached to an intermediate elastic element that is attached to an article.

The tab portion may be unitary with the article to which it is attached or may be a separate element joined directly to the article, as shown in FIGS. 8–10, or joined to an intermediate functional or nonfunctional substrate as shown in FIG. 13. In the FIG. 13 embodiment, a tab portion 65 is point bonded 62 at a portion 61 of the tab substrate to an elastic element 66 having inelastic portions and an intermediate elastic portion 67. The elastic element 66 is then joined at an inelastic portion 68 to an article 69. A tab portion may be joined to the article at any suitable location. In a disposable absorbent article embodiment, the tab portion may be an extension of the material making up the side panel.

In such cases, it may be preferable to provide additional material on the side panel or to process the material of the side panel so as to change some of its physical properties. The tab portion may be made of the same or different materials than the article to which it is attached, making it easy to match the exact properties of the fastening device to the intended use. Further, the material from which the tab portion and/or tab member is made can be reinforced and/or weakened at certain locations to help provide the desired flexibility and stiffness to the fastening portion tab member and tab substrate. Methods of weakening the material include scoring, cutting, thinning, bending, heat treating, chemical treating and the like. Methods of reinforcing include heat or chemical treating the material, adding material, and increasing the thickness and the like.

Figure 11:
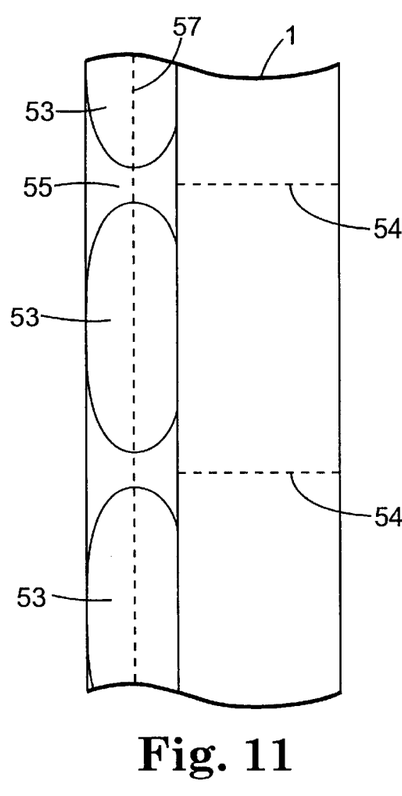
FIG. 11 is a top view of an invention tab portion partially cut from a precursor web.
Figure 12:
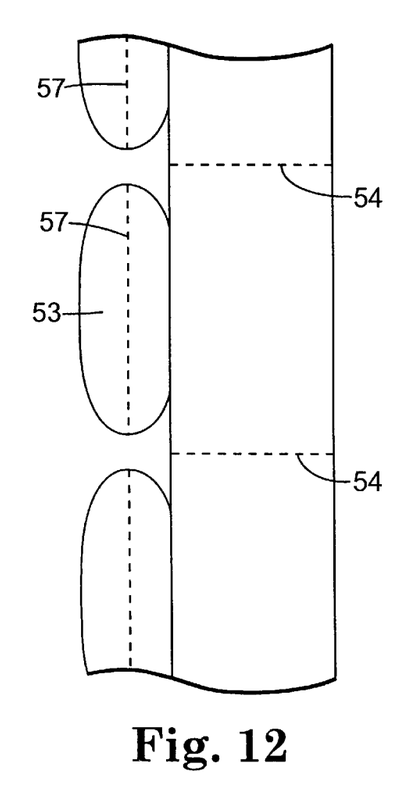
FIG. 12 is a top view of an invention tab portion fully cut from a precursor web.

FIGS. 3–7 are preferred embodiments of a precursor webs 1 of the invention tab portion structure, prior to formation of the discrete tab portions which are generally formed by cutting the desired shape from the precursor web. At least a semi-flexible tab substrate web 2 is provided. The substrate web 2 can generally have a Gurley stiffness of 1–1000 and is preferably formed of a nonwoven, woven or film, or laminate thereof. The overall tab substrate 12 or 22 (formed by one or more layers of the tab substrate web 2 as shown in FIGS. 3–7) could have a Gurley stiffness of from 1 to 5000 and preferably 2 to 500, when used alone or in combination with other substrates or materials. As shown in FIG. 6, onto the substrate web 2 in the tab member portion can be placed a tab member reinforcement element 23 which could have a rigidity substantially higher than that of the substrate web 2. Generally the substrate web 2 and an optional tab reinforcement element 23, has a Gurley stiffness so as to provide that at least the formed lip portion 6 of the tab member 3 has a Gurley stiffness of from 500 to 8000, preferably 1000 to 5000. The tab member 3 can have a Gurley stiffness equal to or preferably at least two (2) times higher than that of the tab substrate alone, or laminates including the substrate web 2, preferably at least five (5) times greater. The optional tab reinforcement element 23 is preferably formed out of a thermoplastic polymer which generally would have a thickness of from 0.1 mm to 1.0 mm, preferably 0.2 mm to 0.8 mm. The tab member 3 also preferably has a tensile load at yield between 50 and 250 Newtons for a cross-sectional area of about 8 mm$^2$ and an elongation at yield of between 2% and 20%. The precursor web is cut into suitable tab portions as is shown in FIGS. 11 and 12. The individual tab members 53 are created by removing portions 55. The pivot regions 57 are created by the folding. Individual tab portions are separated or separable from the precursor substrate along cut lines 54, which can be serrated or continuous cut lines.

Figure 14:
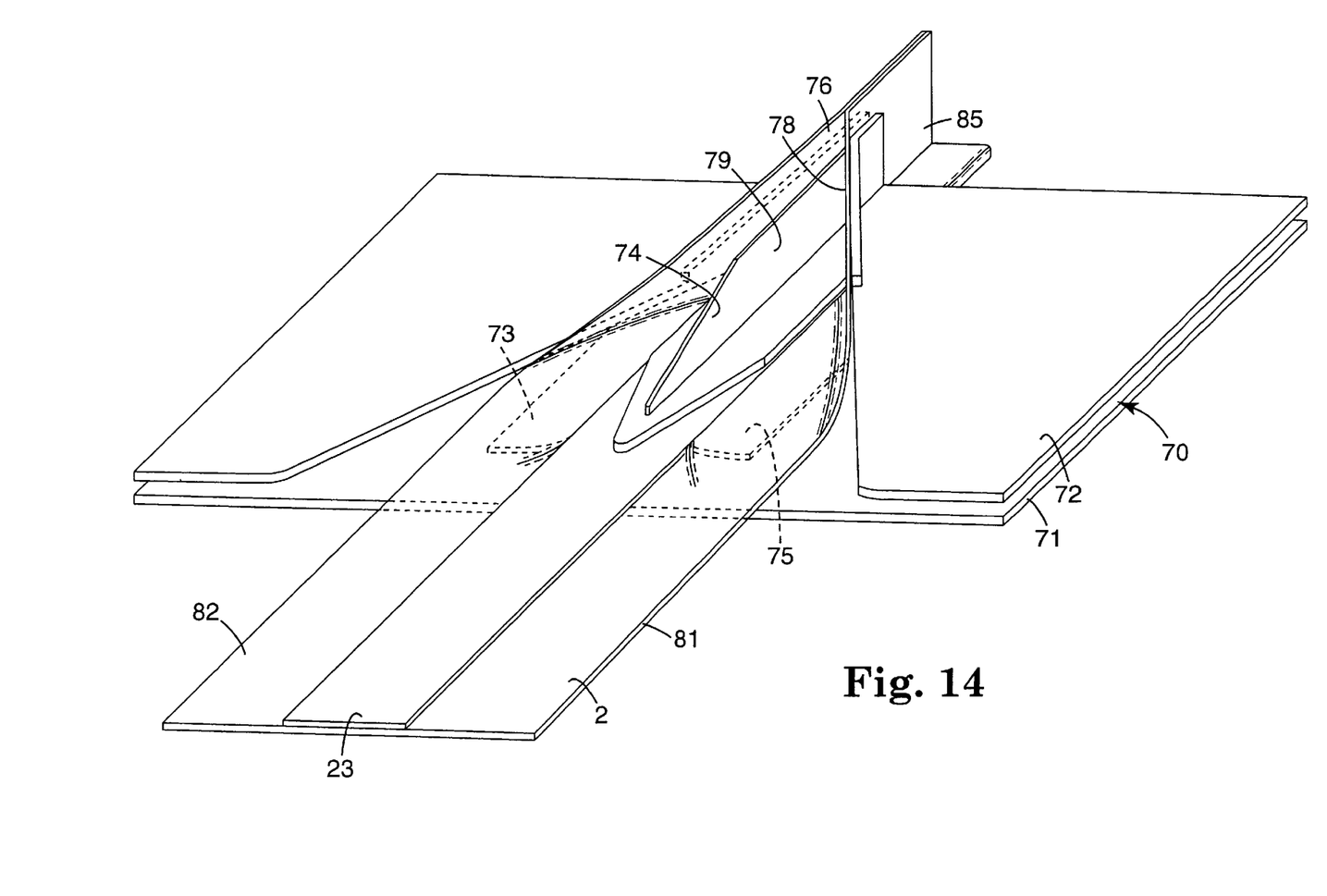
FIG. 14 is a schematic view of a folding apparatus for preparing the fourth embodiment tab portion of the invention.

FIG. 14 shows a folding apparatus and method for forming the precursor web of the fourth embodiment of the invention shown in FIG. 6. A substrate web 2, preferably previously coated with a pressure-sensitive adhesive, is fed with a reinforcement element 23 material into a folding jig 70. The folding jig 70 has a bottom plate 71 and a top plate 72 and a tongue element 74. The bottom face has guide rails 73 and 75 to accommodate the reinforcing element material which is forced into the gap, formed between the rails, by the tongue 74. This forces the end portions 81 and 82 of the substrate web 2 up to engage side rails 76 and 78 provided in the jig top plate 72. The tongue is also provided with a optional rail 79 to keep the adhesive coated substrate web apart until it is in the bonding region 85 of the jig 70, where the tongue terminates to allow the desired folded adhesive coated portions of the substrate web to come together and bond. The portions of the jig 70 in contact with adhesive coated portions of the substrate web 2 will preferably be release coated, such as with Teflon™ type materials.

The tab reinforcement element 23 shown in FIG. 6 can be in the form of the final tab member 3 and have an outer edge 24 and an inner edge 25 and ends 28. The outer edge 24 is designed for insertion into a corresponding slot member 14 as disclosed in U.S. Pat. No. 6,251,097 and the inner edge 25 forms in part the lip portions 6 which engage the outboard portion 15 of the slot member when tension is applied to the tab portion in a plane corresponding to the tab substrate and/or the tab portion. Pivot point or region 27 is located between the outer edge 24 and the inner edge 25 adjacent the lip portion 6 and is designed to allow at least the lip portion to move out of the plane with the tab carrier substrate 22 to create a V-shaped gap between the tab substrate 22 and the lip portion 6. The lip portion 6, when out of the plane with the tab substrate 22, engages with the slot structure as shown in FIG. 2. Generally, the lip portion extends at least 3 mm preferably 3 to 10 mm from the pivot point or region 7 or 27, most preferably 4 to 8 mm. The portion of the tab member opposite the lip portion, along the pivot region, also preferably will extend at least 2 mm, preferable 3 to 15 mm, from the pivot region, and generally would be at least 20 percent of the lip portion width, preferable at least 50 percent of the lip portion width. This is to provide rotational stability to the engaged tab member, so that when the lip portion is engaged it does not release by rotating around the engaged portion of the slot member when shear forces are applied.

At least one layer of the tab substrate 12 or 22 is continuous with a layer forming the tab member 3. For all constructions, preferably one layer 2, forming a layer of both the tab substrate and the tab member, extends over substantially all the tab member, forming both the outer surface 31 of the tab member 3 and the lower surface 32 of the tab member lip portion 6. This lower surface 32 also forms the upper surface of the V-shaped gap as a portion of the tab substrate 12 or 22. This single layer also preferably forms the lower surface 34 of the outer edge region of the tab member and a surface of the tab substrate 12 or 22 over at least a portion of the tab substrate 12 or 22. This allows the tab construction to be stable and provide secure attachment of the tab member to the tab substrate without the need for additional attachment elements such as adhesives, thermal bonding or the like. The invention folded tab construction is also easy to manufacture by simple folding and laminating techniques. The pivot point or region can be formed by a fold line 36 of the substrate web 2. The pivot point or region could also be formed by bonding the substrate web layer 2 by heat or ultrasonics at the desired point of the pivot point, if the pivot point is not formed by a fold line 36. In this case, the fold line 36 could extend into the terminal region 34 of the tab member 3 up to the outer edge 4, which outer edge 4 can also be a fold line 37 of the substrate web 2.

In certain preferred embodiments, as shown in FIGS. 3 and 6 (also 7–10), the substrate web 2 is coated with a heat activated or pressure-sensitive adhesive 33, over all or a portion of the web, to allow the folded portions of the substrate web to adhere to each other and to other provided elements, such as the tab reinforcement element 23 (as in FIG. 6) or the article 40. The adhesive where present would bond adjacent layers of the substrate web which would increase the Gurley stiffness at these bonded regions. Alternatively, folded portions of the substrate web could also be heat or sonically bonded at desired locations as shown in FIGS. 4 and 5. The bonding of the substrate web is preferably continuous in at least the tab member of the tab portion. In the tab substrate, continuous bonding is not necessary as this region of the tab portion is preferably less stiff. As such, bonding in the tab substrate can be intermittent by intermittent adhesive bonding or intermittent thermal type bonding. The tab substrate could also be continuously bonded and then selectively weakened, as described above, to decrease stiffness, if desired.

The slot member 14 is similarly provided with a substrate web, which has flexibility similar to the tab substrate 12 of the tab portion 11. Preferably, the slot 18 includes a rigidifying element 13 around its periphery, which provides for easier insertion of the tab member 3 and more secure engagement with the tab member 3 lip structure 6 and further defines the slot member outboard and inboard portions 15 and 16. The outboard portion 15 of the slot 18 engages at least one lip portion 6 when the slot member 14 and/or tab portion is placed under tension. The outer edge 4 of the tab member 3 is preferably curved or likewise tapered to allow for easier insertion into the slot 18. Similarly, the lip portion 6 is preferably curved or the like at the side edges of the lip portion to ease the initiation of the gripping action with the outboard portion 15 of the slot 18.

The optional tab reinforcement element 23 in the tab members can be joined to the substrate web 2 by the use of adhesives, thermal or ultrasonic bonding, or by melt lamination of thermoplastic tab substrate material preferably onto porous substrate web(s). The substrate web 2 as shown is a single web but this web could be a laminate having one or more layers. The web is folded to form the tab portion with the optional tab reinforcement element. The tab reinforcement element 23 could be a thermoplastic film layer or alternatively, woven or film-like materials or laminates.

Figure 7:
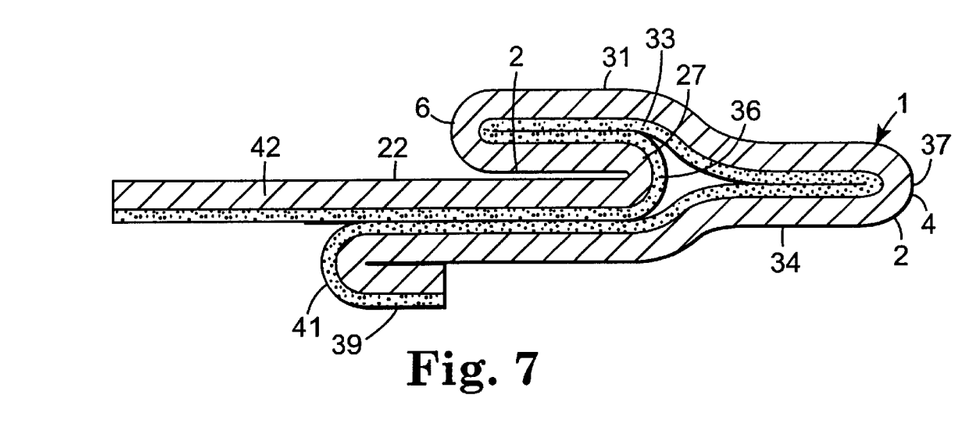
FIG. 7 is a cutaway top view of a fifth embodiment precursor web from which the invention tab portions are cut.

FIG. 7 shows an alternative embodiment of the FIG. 3 embodiment where a further fold line 41 has been provided creating an unattached portion 43. As shown in FIGS. 8, 9 and 10, this unattached portion 39 can then be attached to an article 40 creating a secure two-sided bond or Y-bond. In this case, the entire tab portion is attached to both sides of an article 40 by unattached portion 43 and non-laminated portion 42 of the substrate web 2. Where these portions (39 and 42) are covered by adhesive the attachment can be easily accomplished by application of pressure or heat. Alternatively heat or sonic bonding or the like could be used, with an embodiment such as shown in FIG. 4.

The substrate webs 2 which can be used in connection with the present invention may have a variety of constructions. For example, the substrates may be a woven material, nonwoven material, knit material, paper, film, or any other continuous media. The substrates may have a wide variety of properties, such as extensibility, elasticity, flexibility, conformability, breathability, porosity, stiffness, etc. Further, the substrates may include pleats, corrugations or other deformations from a flat planar sheet configuration.

Suitable processes for making a nonwoven web that may be used in connection with the present invention include, but are not limited to, airlaying, spunbond, spunlace, bonded melt blown webs and bonded carded web formation processes. Spunbond nonwoven webs are made by extruding a molten thermoplastic, as filaments from a series of fine die orifices in a spinneret. The diameter of the extruded filaments is rapidly reduced under tension by, for example, by non-eductive or eductive fluid-drawing or other known spunbond mechanisms, such as described in U.S. Pat. Nos. 4,340,563; 3,692,618; 3,338,992 and 3,341,394; 3,276,944; 3,502,538; 3,502,763 and 3,542,615. The spunbond web is preferably bonded (point or continuous bonding).

The nonwoven web layer may also be made from bonded carded webs. Carded webs are made from separated staple fibers, which fibers are sent through a combing or carding unit which separates and aligns the staple fibers in the machine direction so as to form a generally machine direction-oriented fibrous nonwoven web. However, randomizers can be used to reduce this machine direction orientation.

Once the carded web has been formed, it is then bonded by one or more of several bonding methods to give it suitable tensile properties. One bonding method is powder bonding wherein a powdered adhesive is distributed through the web and then activated, usually by heating the web and adhesive with hot air. Another bonding method is pattern bonding wherein heated calender rolls or ultrasonic bonding equipment are used to bond the fibers together, usually in a localized bond pattern though the web can be bonded across its entire surface if so desired. Generally, the more the fibers of a web are bonded together, the greater the nonwoven web tensile properties.

Airlaying is another process by which fibrous nonwoven webs useful in the present invention can be made. In the airlaying process, bundles of small fibers usually having lengths ranging between about 6 to about 19 millimeters are separated and entrained in an air supply and then deposited onto a forming screen, often with the assistance of a vacuum supply. The randomly deposited fibers are then bonded to one another using, for example, hot air or a spray adhesive.

Meltblown nonwoven webs may be formed by extrusion of thermoplastic polymers from multiple die orifices, which polymer melt streams are immediately attenuated by hot high velocity air or steam along two faces of the die immediately at the location where the polymer exits from the die orifices. The resulting fibers are entangled into a coherent web in the resulting turbulent airstream prior to collection on a collecting surface. Generally, to provide sufficient integrity and strength for the present invention, meltblown webs must be further bonded such as by through air bonding, heat or ultrasonic bonding as described above.

A web can be made extensible by skip slitting as is disclosed in, e.g., International Publication No. WO 96/10481. If an elastic, extensible web is desired, the slits are discontinuous and are generally cut on the web prior to the web being attached to any elastic component. Although more difficult, it is also possible to create slits in the nonelastic web layer after the nonelastic web is laminated to the elastic web. At least a portion of the slits in the nonelastic web should be generally perpendicular (or have a substantial perpendicular vector) to the intended direction of extensibility or elasticity (the at least first direction) of the elastic web layer. By generally perpendicular it is meant that the angle between the longitudinal axis of the chosen slit or slits and the direction of extensibility is between 60 and 120 degrees. A sufficient number of the described slits are generally perpendicular such that the overall laminate is elastic. The provision of slits in two directions is advantageous when the elastic laminate is intended to be elastic in at least two different directions.

A nonwoven web used in connection with the present invention can also be a necked or reversibly necked nonwoven web as described in U.S. Pat. Nos. 4,965,122; 4,981,747; 5,114,781; 5,116,662; and 5,226,992. In these embodiments the nonwoven web is elongated in a direction perpendicular to the desired direction of extensibility. When the nonwoven web is set in this elongated condition, it will have stretch and recovery properties in the direction of extensibility.

The tab reinforcement elements are preferably formed of a wide variety of different thermoplastic material and preferably nonelastomeric thermoplastic polymeric materials. As used in connection with the present invention, "thermoplastic" (and variations thereof) means a polymer or polymeric composition that softens when exposed to heat and returns to its original condition or near its original condition when cooled to room temperature. Preferred thermoplastic compositions are those that are melt processable. Such polymers are those that will flow, yet not significantly degrade during a melt process. Some examples of nonelastomeric thermoplastic compositions that may be used include, but are not limited to, polyurethanes, polyolefins (e.g., polypropylenes, polyethylenes, etc.), polystyrenes, polycarbonates, polyesters, polymethacrylates, ethylene vinyl acetate copolymers, ethylene vinyl alcohol copolymers, polyvinylchlorides, acrylate modified ethylene vinyl acetate polymers, ethylene acrylic acid copolymers, nylons, fluorocarbons, or blends or copolymers thereof, etc. A nonelastomeric thermoplastic polymer is one that melts and returns to its original condition or near its original condition upon cooling and which does not exhibit elastomeric properties at ambient conditions (e.g., room temperature and pressure). As used in connection with the present invention, "nonelastomeric" means that the material will not substantially resume its original shape after being stretched. Further, the nonelastomeric materials may preferably sustain permanent set following deformation and relaxation, which set is preferably at least about 20 percent or more, and more preferably at least about 30 percent or more of the original length at moderate elongation, e.g., about 50% (for those materials that can even be stretched up to 50% without fracture or other failure).

What is claimed is:

1. A fastening tab laminate for use in a slot and tab closure system comprising a tab portion having a tab member and a tab substrate wherein the tab member has a outer edge and an inner edge, the inner edge forming at least one lip portion, the tab member and at least a portion of the tab substrate and the tab members are formed from at least one folded substrate web which substrate web within the tab member is permanently bonded to itself or an optional tab reinforcement element and wherein the lip portion is pivotable from the tab substrate such that it can pivot away from the tab substrate.

2. The fastening tab laminate of claim 1 wherein the at least one flexible substrate web is a porous web.

3. The fastening tab laminate of claim 2 wherein the at least one flexible substrate web is a nonwoven fibrous web.

4. The fastening tab laminate of claim 2 wherein there is a tab reinforcement formed of is a thermoplastic polymer material.

5. The fastening tab laminate of claim 4 wherein the rigid tab substrate thermoplastic material is at least partially penetrated into the porous structure of the flexible substrate web.

6. The fastening tab laminate of claim 5 wherein the at least one flexible substrate web forms the tab members with at least one outer fold and at least one inner fold with said outer fold and said inner fold forming the lip portion, the same at least one substrate web further forms at least a portion of the tab substrate.

7. The fastening tab laminate of claim 6 wherein the substrate web has at least two outer folds forming the tab member outer edge and inner edge.

8. The fastening tab laminate of claim 6 wherein the substrate web is coated with adhesive in at least the portions forming the tab member.

9. The fastening tab laminate of claim 8 wherein the adhesive is as pressure-sensitive adhesive.

10. The fastening tab laminate of claim 1 wherein the substrate web is adhesively laminated.

11. The fastening tab laminate of claim 1 wherein at least one elastic element is attached to the substrate web forming the tab substrate so as to provide an elastic fastening tab laminate.

12. The fastening tab laminate of claim 4 wherein the tab reinforcement has a curved outer edge.

13. The fastening tab laminate of claim 12 wherein the lip portion extends at least 3 to 10 mm from a pivot point or region.

14. The fastening tab laminate of claim 1 wherein the tab member has a Gurley stiffness of from 500 to 8000.

15. The fastening tab laminate of claim 14 wherein the tab substrate has a Gurley stiffness of from 1 to 500.

16. The fastening tab laminate of claim 15 wherein the tab member has a Gurley stiffness at least two times greater than that of the tab substrate.

* * * * *